US00PP10131P

United States Patent [19]

Dümmen

[11] Patent Number: Plant 10,131

[45] Date of Patent: Nov. 25, 1997

[54] NEW GUINEA IMPATIENS PLANT NAMED 'DUECONTO'

[75] Inventor: Marga Dümmen, Rheinberg-Eversael, Germany

[73] Assignee: Dümmen Jungpflanzenkulturen, Rheinberg-Eversael, Germany

[21] Appl. No.: 665,250

[22] Filed: Jun. 17, 1996

[51] Int. Cl.[6] ..... A01H 5/00

[52] U.S. Cl. ..... Plt./87.6

[58] Field of Search ..... Plt./87.6

[56] References Cited

PUBLICATIONS

UPOVROM Disk 1997/01 Result Sheet "Dueconto", 1997.

*Primary Examiner*—James R. Feyrer
*Assistant Examiner*—Kent L. Bell
*Attorney, Agent, or Firm*—C. A. Whealy

[57] ABSTRACT

A new and distinct cultivar of New Guinea Impatiens plant named 'Dueconto', characterized by its salmon pink flowers; floriferousness; early flowering; flowers that are resistant to rain damage; compact growth habit; freely branching plant habit; and dark green and satiny non-variegated foliage.

1 Drawing Sheet

The present invention relates to a new and distinct cultivar of New Guinea Impatiens plant, botanically known as *Impatiens hawkeri*, named 'Dueconto'. It is anticipated that the plant of this application will be marketed under the Trademark "HWD Concerto". Accordingly, the plant of this application may be referred to as "HWD Concerto" 'Dueconto' in the market place.

The new cultivar is a product of a planned breeding program conducted by the inventor in Rheinberg, Germany. The objective of the breeding program was to develop a new salmon pink-flowered variety that was freely branching; compact in growth habit; flowered early; and with flowers resistant to rain damage.

The new cultivar originated from a cross made by the inventor of the cultivar 'Aruba' (disclosed in U.S. Plant Pat. No. 8,456) as the male or pollen parent with the cultivar 'Delias' (disclosed in U.S. Plant Pat. No. 7,838) as the female or seed parent.

The cultivar 'Dueconto' was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Impatiens are stable and reproduced true to type in successive generations of asexual reproduction.

The following traits have been repeatedly observed and are determined to be the unique characteristics of 'Dueconto'. These characteristics in combination distinguish 'Dueconto' as a new and distinct cultivar:

1. Salmon pink flowers.
2. Numerous flowers per plant.
3. Early flowering.
4. Flowers that are resistant to rain damage.
5. Compact growth habit.
6. Freely branching plant habit.
7. Dark green and satiny non-variegated foliage.

In comparison to plants of the parent cultivar Aruba, plants of the new Impatiens have a more compact growth habit and flower earlier. Additionally, plants of the new Impatiens have salmon pink flowers whereas plants of the cultivar Aruba have blue purple flowers. Compared to plants of the parent cultivar Delias, plants of the new Impatiens have larger flowers, flower earlier, and are more compact. Additionally plants of the new Impatiens have salmon pink flowers whereas plants of the cultivar Delias have medium pink flowers.

The accompanying colored photograph illustrates the overall appearance of the new cultivar, showing the colors as true as it is reasonably possible to obtain in colored reproductions of this type.

The photograph comprises a top perspective view of a typical potted plant of 'Dueconto' with one plant in a 12-cm container.

Some of the flowers in the photograph appear darker in color than the actual flower color due to light reflectance.

The cultivar 'Dueconto' has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 28° C. and night temperatures of 20° to 22° C. and light levels of 30,000 to 40,000 lux.

In the following description, color references are made to The Royal Horticultural Society Colour Chart except where general terms of ordinary dictionary significance are used.

Classification:

*Botanical.*—*Impatiens hawkeri.*

*Commercial.*—New Guinea Impatiens.

*Cultivar.*—'Dueconto'.

Parentage:

*Male parent.*—Cultivar 'Aruba' (disclosed in U.S. Plant Pat. No. 8,456).

*Female parent.*—Cultivar 'Delias' (disclosed in U.S. Plant Pat. No. 7,838).

Propagation:

*Type cutting.*—Terminal cuttings.

*Time to initiate roots.*—Summer, 27C: About 21 days. Winter, 20C: About 28 days.

Plant Description:

*General appearance.*—Rounded; dense; freely branching and compact growth habit; upright and spreading; moderate growth rate; suitable for 10 to 12-cm pots.

*Plant height.*—16 to 17 cm from soil level to top of plant plane.

*Foliage description.*—Shape: Elliptic with acuminate tip and attenuate base. Size: Length: 9.5 to 11 cm. Width: 3.2 to 4 cm. Texture: Smooth, satiny, and glabrous. Margin: Finely serrated, ciliate. Petiole length: 1 to 1.5 cm. Color: Young foliage, upper surface: Darker than 137A. Young foliage, under surface: 147B. Mature foliage, upper surface: Darker than 137A. Mature foliage, under surface: 147B. Veins, upper surface: Midvein dark purple, 59A, laterals, 147B. Veins, under surface: Midvein, 146D, laterals, 146A. Petiole: 147C/147D under side with dark pink, 63B, on upper side.

*Stem description.*—Internode length: 4 to 5 cm. Stem color: More mature stems, green, 146C. Younger stems are purple, 59A.

Flower description:

*Flowering habit.*—Freely flowering.

*Natural flowering season.*—Year-round. Under summer conditions, plants flower 6 to 7 weeks after planting; under winter conditions, plants flower 9 to 11 weeks after planting.

*Flowers born.*—Flower buds develop in apical leaf axils. Open flowers are displayed above the foliage.

*Quantity of inflorescences.*—Very floriferous; usually 17 to 19 buds and open flowers per axil.

*Flower longevity on plant.*—From opening, flowers will last 7 to 12 days.

*Flower diameter.*—About 6 cm.

*Flower depth (height).*—1.5 to 2 cm.

*Petals.*—Shape: Cordate. Quantity, arrangement: 5 petals overlapping. Aspect: Flat. Size: Length: About 3.1 cm. Width: About 3.5 cm. Texture: Smooth, satiny, and glabrous. Margin: Entire. Color: When opening: 52B. Upper surface: Iridescent, 52C. Small red purple, 57A, eye and lighter red purple, 57D, streaks and flecks. Under surface: 58C. Small red purple, 57A, eye and lighter red purple, 57D, streaks and flecks.

*Peduncle.*—Angle. Erect. Length: About 4 cm. Color: Proximal, 144B, distal, 59B.

*Flower bud.*—Shape: Ovoid with spur. Length: About 1.5 cm. Diameter: About 1 cm. Color: 59A.

*Spur.*—Shape: Needle-shaped, curved at end. Color: 45A/46A/185A.

*Sepals.*—Arrangement: Opposite. Quantity: 2. Shape: Ensiform with acuminate tip. Texture: Shiny, smooth and glabrous. Margin: Entire. Color: Upper side: Proximal, 145C/145D, distal, 66C. Under side: Proximal, 145C/145D, distal, 66C.

*Reproductive organs.*—Androecium: Stamen number: 5. Anther color: 57C. Pollen color: 11D. Gynoecium: Ovary color: 144A.

Disease resistance: No fungal, bacterial nor viral problems observed.

Seed development: Seed production is very rarely observed.

It is claimed:

1. A new and distinct cultivar of New Guinea Impatiens plant named 'Dueconto', as illustrated and described.

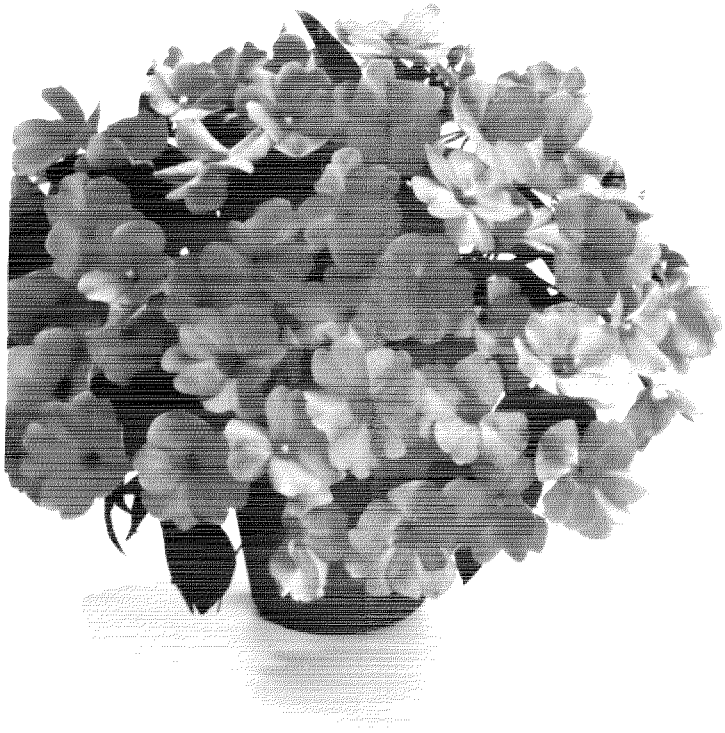

* * * * *